United States Patent [19]

Pippin et al.

[11] Patent Number: 4,708,647
[45] Date of Patent: Nov. 24, 1987

[54] PERIODONTAL PROBE INSTRUMENT

[75] Inventors: David J. Pippin, Shawnee; Diana J. Stindt, Prairie Village, both of Kans.

[73] Assignee: The Curators of the University of Missouri, Columbia, Mo.

[21] Appl. No.: 837,150

[22] Filed: Mar. 7, 1986

[51] Int. Cl.⁴ .............................................. A61C 3/00
[52] U.S. Cl. .................................................... 433/32
[58] Field of Search ............. 128/774, 776; 33/174 D; 433/72, 32

[56] References Cited

U.S. PATENT DOCUMENTS

| | | | |
|---|---|---|---|
| 3,058,225 | 10/1962 | Ward | 33/172 |
| 3,559,292 | 2/1971 | Weissman | 33/169 |
| 3,943,914 | 3/1976 | Grenfell et al. | 33/174 |
| 4,250,895 | 2/1981 | Lees | 433/72 |

Primary Examiner—Robert Peshock
Attorney, Agent, or Firm—Kokjer, Kircher, Bradley, Wharton, Bowman & Johnson

[57] ABSTRACT

A periodontal probe instrument for measuring the depth of the gingival sulcus and periodontal pockets. A probe extending from a handle of the instrument includes a transparent portion which is insertable into the periodontal pocket. An optical fiber extends through the probe and may be retracted until its end is barely visible at the gingival line. A potentiometer driven by the retraction mechanism for the fiber generates an electrical output signal having a voltage proportional to the position of the fiber to provide a measure of the pocket depth. The signal is used to digitally display and print each measurement that is taken.

19 Claims, 5 Drawing Figures

U.S. Patent  Nov. 24, 1987  4,708,647
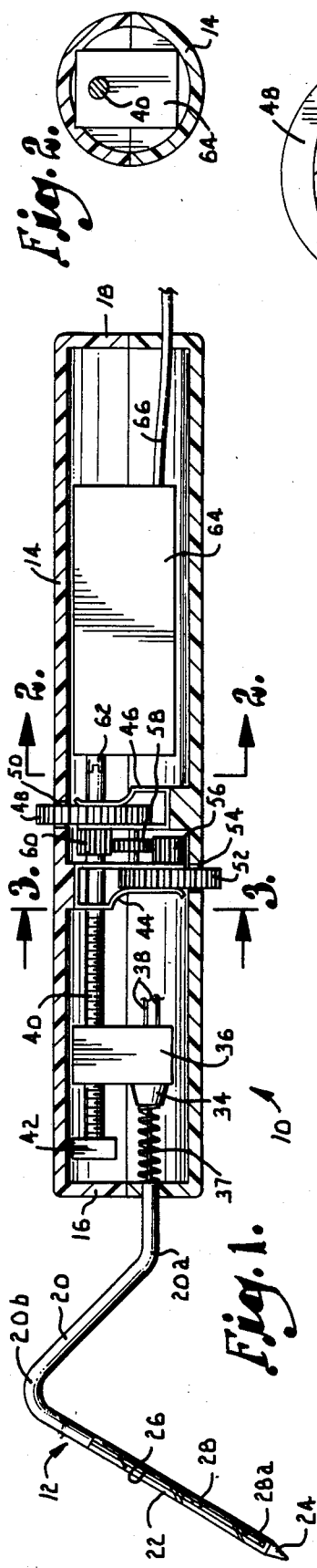
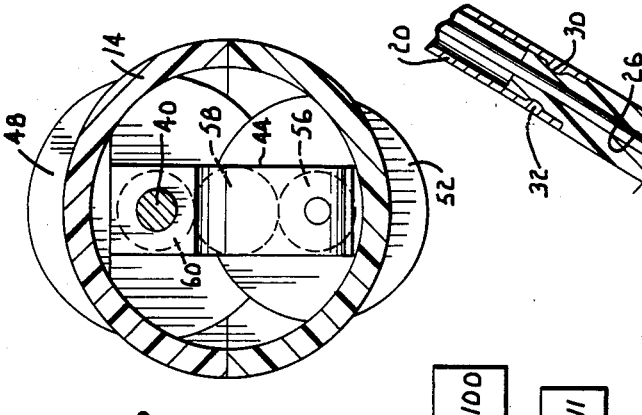
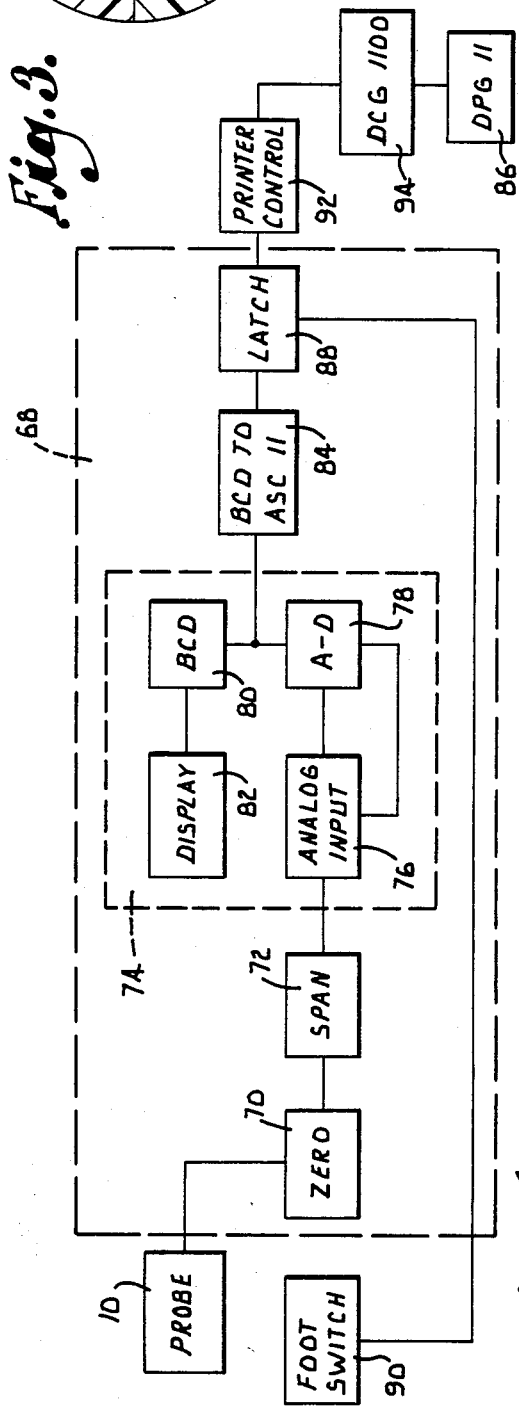

PERIODONTAL PROBE INSTRUMENT

BACKGROUND OF THE INVENTION

This invention relates in general to periodontics and more particularly to an instrument used to measure the depth of the gingival sulcus and periodontal pockets.

Chronic periodontal disease is typically a plaque induced inflammatory disease which results in progressive bone loss around the teeth. The increased sulcus depths in the gums create periodontal pockets which are indicative of the progression of the disease. To adequately diagnose and treat periodontal disease, it is essential to assess past periodontal destruction and to monitor current disease activity. This requires that the depths of the gingival sulcus and any periodontal pockets be accurately determined. At present, pocket depth is normally measured by a periodontal probe in the form of a metal device having a thin tip which is scored with calibration marks. The probe is inserted into the sulcus between each tooth and the gingiva until resistance is felt, which indicates that the bottom of the periodontal pocket has been reached by the tip of the probe. The depth reading is then taken by noting the penetration of the probe, as visually gauged by the calibration mark which is judged to be closest to the height of the gingival margin. Standard practice involves taking six depth readings around each tooth at prescribed locations. Each reading is recorded, typically by verbally reporting it to an assistant who writes it by hand on a dental chart.

As can easily be appreciated, the use of a conventional periodontal probe is a time consuming and labor intensive procedure which does not always result in the precise recording of measurements. Highly paid technicians must spend a considerable amount of time in making a visual reading of the pocket depth each of the six times the probe is inserted around each tooth, and additional time is consumed by the need to manually record each reading. Larger errors are not uncommon because the probe is normally calibrated in increments as large as 3 millimeters, and this necessitates visual interpolation between the calibration marks. Human error that is inevitably involved in visually taking and interpolating the readings adds to the inaccuracy, as does the error that sometimes results from the verbal reporting and manual writing of the readings. The lack of precision in the measurements that result from use of the conventional probe can lead to inaccurate diagnoses, improper therapy, and other adverse consequences.

SUMMARY OF THE INVENTION

Due to the aforementioned problems associated with conventional periodontal probes, it is readily apparent that a need exists for a probe that is improved in its accuracy and ease of use. The present invention is aimed primarily at meeting this need.

More specifically, it is an important object of the invention to provide a periodontal instrument that can be used more quickly and easily than the probes that have been available in the past. With respect to ease of use, it is an important feature of the invention that the depth reading is visually displayed and may be automatically printed simply by activating a switch. Because there is no need to manually record each reading, the time consumed in using the probe is significantly reduced.

Another important object of the invention is to provide a periodontal instrument that is more accurate and repeatable than the probes that have been used in the past. Since there is no need to visually gauge the penetration of the probe in relation to calibration marks, the incidence of human error is reduced markedly. Moreover, the instrument prints out each depth figure to eliminate the possibility of inaccurate figures occurring as a result of recording the readings by hand in accordance with past practice.

A further object of the invention is to provide a periodontal instrument in which an optical fiber is used to provide a clear and readily visible indication of the depth of penetration of the probe. This feature enhances both the accuracy and the ease with which the instrument is used.

An additional object of the invention is to provide a periodontal instrument in which physical movement of the optical fiber is automatically and accurately translated into an electrical signal which is used to digitally display and to print out each measurement figure and bleeding points.

Still another object of the invention is to provide, in a periodontal instrument of the character described, a handle which permits the probe to be easily and conveniently manipulated as required while maintaining good tactile sensitivity.

Yet another object of the invention is to provide a periodontal probe of the character described in which the components are inert and resistant to alcohol, moisture, blood, saliva and other mouth fluids.

A further object of the invention is to provide a periodontal instrument which is able to produce a printed, adhesive record of all of the probing measurements on a typically stylized dental chart.

An additional object of the invention is to provide a periodontal instrument of the character described which can be used safely without presenting an electrical shock hazard.

A still further object of the invention is to provide in a periodontal instrument of the character described, a probe having a tip portion which is replaceable.

Yet another object of the invention is to provide a periodontal instrument of the character described having components that are simple and economical to fabricate.

An additional object of the invention is to provide an instrument that is constructed to allow the operator to distinguish between pocket measurements which bleed upon probing and those which do not, and which identifies each on the printed record and quantifies them into a bleeding index score which is displayed and recorded.

A still further object of the invention is to provide a periodontal instrument of the character described which is suitable to undergo cold sterilization.

Other and further objects of the invention, together with the features of novelty appurtenant thereto, will appear in the course of the following description.

DESCRIPTION OF THE DRAWING

In the accompanying drawing, which forms a part of the specification and is to be read in conjunction therewith, and in which like reference numerals are used to indicate like parts in the various views:

FIG. 1 is a side elevational view of a periodontal instrument constructed according to a preferred embodiment of the present invention, with the handle of the instrument shown in section to illustrate the internal components;

FIG. 2 is a sectional view taken through the handle generally along line 2—2 of FIG. 1 in the direction of the arrows;

FIG. 3 is a sectional view on an enlarge scale taken through the handle generally along line 3—3 of FIG. 1 in the direction of the arrows;

FIG. 4 is a fragmentary sectional view on an enlarge scale showing a portion of the probe of the periodontal instrument, with the break lines indicating continuous length of the transparent portion of the probe and the optical fiber it contains; and FIG. 5 is a block diagram of the electronic circuitry included in the periodontal instrument.

DETAILED DESCRIPTION OF THE INVENTION

Referring now to the drawing in more detail and initially to FIG. 1, numeral 10 generally designates a periodontal instrument constructed in accordance with the present invention. The instrument 10 includes a probe 12 which extends from a hollow handle 14 containing the main operating components of the instrument. The handle 14 is generally cylindrical and is approximately the size of an ordinary pencil in order to be easily held in the hand for manipulation of the probe 12. The handle 14 has closed front and back ends 16 and 18, respectively, and the probe 12 extends through the front end 16.

The probe 12 includes a metal tube 20 which extends from end 16 of the handle and is bent at 20a and 20b into a generally hook shaped configuration. Extending from the distal end of the tube 20 and forming a continuation thereof is a transparent portion 22 of the probe which is constructed of polycarbonate material or any other suitable substance. The free end of the transparent portion 22 is provided with a tapered tip 24 to facilitate insertion of the probe into periodontal pockets. A small longitudinal passage 26 extends centrally through probe 12 and terminates adjacent the tip 24. Probe 12 is approximately 1 millimeter in diameter.

Received closely in passage 26 for axial extension and retraction is an optical fiber 28 having its free end 28a located in the transparent portion 22 of the probe. Fiber 28 extends through tube 20 and into the interior of handle 14. Preferably, the optical fiber 28 has a diameter of approximately 0.250 millimeter.

The transparent portion 22 of probe 12 is preferably held releaseably by the metal tube 20 to permit removal and replacement of the transparent portion. With reference to FIG. 4 in particular, the end of portion 22 opposite tip 24 is reduced somewhat in diameter so that it fits closely in the open adjacent end of tube 20. The reduced diameter end of portion 22 is provided with an annular groove 30 which closely receives an annular bead 32 which projects inwardly from the wall of tube 20 adjacent its open end. The close fit of bead 32 in groove 30 normally retains portion 22 in place on tube 20. Sufficient force exerted to pull portion 22 away from tube 20 displaces groove 30 from the bead 32 and permits portion 22 to be detached from the tube and replaced by another transparent portion of the probe.

Referring again to FIG. 1, the proximal end of the optical fiber 28 connects with a light emitting diode 34 which is carried on a mounting block 36 located within the handle 14. A spring 37 is coiled around fiber 28 and acts at one end against end 16 of the housing and at the other end against the LED 34. Electrical lines 38 supply power to the LED 34 so that it can be energized to energize the optical fiber 28. When energized by the LED, the optical fiber emits light in order to enhance the visibility of its free end 28a within the transparent portion 22 of the probe.

Within the handle 14, a drive screw 40 extends through and has a threaded connection with the mounting block 36, which carries the LED 34. A bearing 42 receives the end of screw 40 and supports the screw for rotation. The opposite end portion of screw 40 extends through a pair of brackets 44 and 46 secured to the handle 14. A rotatable thumb wheel 48 is fitted on screw 40 and is retained by bracket 46. The periphery of the thumb wheel 48 projects through an opening 50 in handle 14 and is thus accessible so that it can be turned to turn the drive screw 40.

Another thumb wheel 52 is retained by bracket 44 and projects through an opening 54 which is formed in handle 14 at a location diametrically opposite opening 50. Thumb wheel 52 is rotatable and carries a small pinion 56 which mates with and drives a small gear 58. Gear 58 meshes with another pinion 60 that rotates with thumb wheel 48. By this arrangement, the gear train connects the thumb wheels 48 and 52 with one another so that the drive screw 40 is turned whenever either of the thumb wheels is turned. Due to the threaded connection of block 36 with the drive screw 40, block 36 is reciprocated along a linear path when the screw is turned in opposite directions.

It should be noted that the axes of the thumb wheels 48 and 50 can be oriented transversely to the longitudinal axis of handle 14 rather than parallel to it as shown. Such an arrangement permits the thumb wheels to be turned by moving the thumb in a longitudinal direction along handle 14, which is less awkward and more convenient for many operators of the instrument. This orientation of the thumb wheels can be effected by using bevel gears, worm gears or another mechanism. It should be noted that the thumb wheels 48 and 50 can be located on the front end of handle 14, and in such an arrangement, bearing 42, screw 40 and block 38 are all posterior to gears, with the optical fiber passing through the gear mechanism.

The end of screw 40 mates with and drives a shaft 62 that forms the input shaft of a ten turn potentiometer 64 mounted within handle 14. An electrical cable 66 extends from the potentiometer to connect it (and wires 38) with a table mounted base unit 68 (see FIG. 5). When the drive screw 40 is turned to change the position of block 46, the potentiometer 64 is adjusted, and its output voltage is proportional to the position of block 46 along screw 40. Since movement of block 46 extends and retracts the optical fiber 28, the output voltage from the potentiometer 64 provides a measurement of the position of the optical fiber and its free end 28a.

Referring now to FIG. 5, the table mounted base unit 68 includes electronic circuit components which process and make use of the electrical signal provided by the potentiometer 64. Preferably, the tip 24 of probe 12 has a length of approximately one millimeter, so that when the optical fiber 28 is fully extended, its free end is located one millimeter from the point of the tip. The base unit 68 includes a zero adjustment component 70 which is used to provide a zero adjustment so that the unit reads its minimum value, corresponding to a depth of 1 millimeter, when the optical fiber 28 is fully extended into the probe. The zero adjustment may be provided by an operational amplifier wired as a unity difference amplifier.

A span and scale component 72 permits calibration of the signal. When the optical fiber is retracted or withdrawn as far as possible from the free end of the probe, the output voltage from the potentiometer 64 is at the maximum value, and the voltage signal should be calibrated so that its full span reflects the maximum depth measurement desired (such as 12 millimeters, for example). The span and scale block 72 serves to set the scale and span of the output voltage and employs a voltage divider for this purpose. The output from the span and scale block 72 is a calibrated signal which is ready for conversion to digital form for display and printing, as will be explained more fully.

An analog to digital conversion device 74 receives the analog signal and converts it to digital form for display and control of the printer. Device 74 is a commercially available unit available from Analog Devices under the trade designation AD7555, and it includes an analog input block 76 which consists of a buffer amplifier, an integrating amplifier and a comparator. The analog input controls the conversion time for the analog to digital processing and provides reference voltages that are used for calibration and comparison purposes. The analog to digital conversion block 78 supplies an output signal to a binary coded decimal block 80 which codes the signal and applies it to a digital display 82 which provides a digital display of each measurement taken by the instrument. The display may be a conventional liquid crystal display which appears on a face panel of the base unit 68.

The output signal from the analog to digital block 78 is also provided to another block 84 which converts the digital signal from binary coded decimal form into standard binary ASCII equivalents which are acceptable as input signals for a printer 86 which may be a 40 column printer available commercially from Alps Electric (U.S.A.), Inc. under the trade designation DPG11. In order to provide stable signals to the printer, the information output from block 84 is electronically latched during the print operation by a latch circuit 88. The latching operation is activated by a foot switch 90 preferably located so that the operator of the instrument 10 can depress it with the foot to store each measurement into memory for later retrieval for printing operations. Switch 90 preferably includes two different switch mechanisms, as will be explained more fully, and the switches may be located on handle 14 rather than being foot operated. The printer has a control circuit 92 and a logic board 94 containing logic circuitry for providing the necessary printing and paper feed operations.

In use of the periodontal instrument, probe 22 is inserted into each periodontal pocket which is to be measured for depth. When the probe has been inserted until resistance is felt, the tip 24 is located at the bottom of the pocket, and one of the thumb wheels 48 or 52 is then turned in a direction to retract the optical fiber 28 until its free end 28a is barely visible and thus aligned with the gingival margin line. In this position of the optical fiber, the distance between the point of tip 24 and the free end 28a of the optical fiber provides an accurate measurement of the depth of the periodontal pocket. The voltage of the output signal from the potentiometer 64 is directly proportional to this distance and thus is directly proportional to the pocket depth. The signal is suitably calibrated such that the distance measurement is displayed digitally on the visual display 82. The operator can view display 82 to note the figure for the depth measurement, and he or she then depresses switch 90 to latch the measurement into memory. Preferably, one switch mechanism is used if bleeding is detected at the measurement site and the other switch mechanism is used if there is no bleeding. Thus, the presence or absence of bleeding at each site is entered into memory.

The probe 22 can then be withdrawn from the periodontal pocket and inserted at the next sequential location to obtain another depth measurement. Ordinarily, six measurements are taken at prescribed locations for each tooth. After all of the measurements have been taken in a prescribed, sequential manner, the printer control 92 is activated to provide a print out containing a printed record of each measurement, and there is no need to manually record the depth measurements. Consequently, the error involved in manually recording readings is avoided.

Preferably, the printed record is made on a preprinted, adhesive backed dental chart. The pocket depths are conveniently printed in millimeters, and each measurement that had bleeding associated with it will be indicated as such. For example, a dot may be printed over the measurement figure. It is also contemplated that the unit will calculate and print out a bleeding index defined as the number of pockets that bled divided by the total number of pockets probed.

Because the optical fiber 28 is energized by the LED 34, the free end 28a of the fiber is clearly visible, and the fiber can be adjusted until the free end 28a is precisely in alignment with the gingival margin. This avoids the need to align the gingival margin with a calibration mark and enhances the accuracy of the depth measurements accordingly.

The base unit 68 can be equipped with additional functions, including the ability to generate an audible tone after the entry of a reading to signal the operator that a depth reading was received and entered. A switch can be provided on the base unit to permit the tone function to be disabled if the operator so desires.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. A periodontal instrument for measuring the depth of a periodontal pocket in the gingiva adjacent to a tooth, said instrument comprising a periodontal probe having a transparent portion insertable into the pocket and terminating in a tip located at the bottom of the pocket when the probe is inserted therein, said probe having a longitudinal passage therein;

a fiber received in said passage for axial extension and retraction therein, said fiber having a free end;

means for effecting extension and retraction of said fiber in said passage to permit said leading end of the fiber to be retracted until visible at the gingival margin; and means for measuring the distance between said tip of the probe and said free end of the fiber to measure the pocket depth.

2. The instrument of claim 1, wherein said measuring means comprises:

means for generating an electrical signal having a characteristic indicative of the distance between said tip and free end; and means for using said signal to display said distance.

3. The instrument of claim 2, including means for using said signal to print said distance.

4. The instrument of claim 1, wherein said fiber comprises an optical fiber emitting light when energized and including means for energizing said optical fiber.

5. The instrument of claim 1, including:

a handle from which said probe extends, said handle having a size and shape to be held in the hand; and a mounting bracket to which said fiber is attached at an end thereof opposite said free end, said bracket being mounted in the handle for reciprocating linear movement therein and said means for effecting extension and retraction being operable to reciprocate said bracket.

6. The instrument of claim 5, wherein said means for effecting extension and retraction comprises:

a screw mounted for rotation in said housing and having a threaded connection to said bracket; and a thumb wheel connected with said screw to effect turning of the latter when the thumb wheel is turned, said thumb wheel being accessible on said handle to be manually turned.

7. The instrument of claim 6, including:

a second thumb wheel accessible on said handle at a location diametrically opposed to the first mentioned thumb wheel; and gear means in said handle for coupling said first and second thumb wheels for rotation in unison to effect turning of said screw when either thumb wheel is turned.

8. The instrument of claim 6, wherein said measuring means includes:

means for sensing rotation of said screw; and means for generating an electrical signal indicative of the rotation of said screw.

9. The instrument of claim 8, including means for using said signal to digitally display said distance.

10. The instrument of claim 8, including means for using said signal to print said distance.

11. The instrument of claim 1, including:

a handle from which said probe extends, said handle having a size and shape to be held in the hand; and a metal tube portion of said probe between said handle and said transparent portion.

12. The instrument of claim 11, including releaseable means for connecting said transparent portion of the probe with said metal tube portion to permit replacement of the transparent portion.

13. A periodontal probe instrument for measuring and recording the depths of periodontal pocket in the gingiva, said instrument comprising:

a handle having a size and weight to be held in the hand;

a probe extending from said handle and having a size to be inserted into the pockets;

measuring means associated with said probe and operable on command to measure the depth of pocket in which the probe is inserted;

said measuring means comprising a substantially straight transparent portion of said probe having a longitudinal passage therein, said transparent portion terminating in a tip, a fiber received in said passage for axial extension and retraction therein and having a free end located in said transparent portion of the probe for alignment with the gingival margin, means for generating an electrical signal having a characteristic indicative of the distance between said free end of the fiber and said tip of the probe;

switch means for commanding said measuring means to measure the depth of each pocket in which the probe is inserted; and means for printing the measurements for all pockets in which the probe is inserted and commanded to measure.

14. The instrument of claim 13, wherein said measuring means comprises:

a substantially straight transparent portion of said probe having a longitudinal passage therein, said transparent portion terminating in a tip;

a fiber received in said passage for axial extension and retraction therein and having a free end located in said transparent portion of the probe for alignment with the gingival margin; and means for generating an electrical signal having a characteristic indicative of the distance between said free end of the fiber and said tip of the probe.

15. The instrument of claim 13, wherein said fiber is an optical fiber and including means for energizing said optical fiber to enhance the visibility of said free end thereof.

16. A method for measuring the depth of a periodontal pocket in the gingiva adjacent a tooth, said method comprising the steps:

inserting a transparent probe into the pocket until the tip of the probe reaches the bottom of the pocket;

moving a fiber in the probe until a free end of the fiber is aligned with the gingival margin;

sensing the position of the free end of the fiber relative to said tip of the probe; and providing an electrical signal having a characteristic indicative of the distance between the free end of the fiber and the tip of the probe.

17. A method as set forth in claim 17, including the step of using said signal to digitally display said distance.

18. A method as set forth in claim 17, including the step of using said signal to print said distance.

19. A method as set forth in claim 17, wherein said fiber is an optical fiber and including the step of energizing the optical fiber to enhance the visibility of said free end.

* * * * *